(12) United States Patent
Slemker et al.

(10) Patent No.: US 8,444,702 B2
(45) Date of Patent: May 21, 2013

(54) PLUNGER PIN AND MANIFOLD FOR A PROSTHETIC LIMB

(75) Inventors: Tracy C. Slemker, Clayton, OH (US); Paul L. Galloway, Clayton, OH (US); Robert Hoskins, Springboro, OH (US); Steven Steinbarger, Wilmington, OH (US); Ronda Miller, Beavercreek, OH (US)

(73) Assignee: Prosthetic Design, Inc, Clayton, OH (US)

( * ) Notice: Subject to any disclaimer, the term of this patent is extended or adjusted under 35 U.S.C. 154(b) by 0 days.

(21) Appl. No.: 13/088,612

(22) Filed: Apr. 18, 2011

(65) Prior Publication Data

US 2011/0196510 A1  Aug. 11, 2011

Related U.S. Application Data

(62) Division of application No. 12/481,015, filed on Jun. 9, 2009, now Pat. No. 7,927,377.

(60) Provisional application No. 61/131,457, filed on Jun. 9, 2008.

(51) Int. Cl.
*A61F 2/80* (2006.01)

(52) U.S. Cl.
USPC ............................................................ 623/34

(58) Field of Classification Search
USPC ................................................... 623/32–38
See application file for complete search history.

(56) References Cited

U.S. PATENT DOCUMENTS

| 6,334,876 | B1* | 1/2002 | Perkins | 623/34 |
| 6,689,171 | B2* | 2/2004 | Slemker et al. | 623/33 |
| 2003/0023324 | A1* | 1/2003 | Laghi | 623/36 |
| 2012/0109336 | A1* | 5/2012 | Laghi | 623/33 |

* cited by examiner

*Primary Examiner* — Bruce E Snow

(57) ABSTRACT

An elevated vacuum locking system for prosthetic limb. An exemplary embodiment may include a plunger pin mounted to a flexible liner and including a through passage between a location proximate the exterior of the liner and a distal end of the plunger pin; a locking mechanism mounted within the distal end of a socket; a manifold mounted to the exterior of the distal end of the socket and including a cavity adapted to receive the distal end of the plunger pin when the patient's residual limb and the liner are installed into the socket, the manifold including a through passage connecting an interior of the cavity to an exterior fitting; and a vacuum pump operative to withdraw air from the interior of the socket via the through passage of the plunger pin, the cavity, and the through passage of the manifold.

16 Claims, 13 Drawing Sheets

US 8,444,702 B2

PLUNGER PIN AND MANIFOLD FOR A PROSTHETIC LIMB

CROSS REFERENCE TO RELATED APPLICATIONS

This application is a division of U.S. application Ser. No. 12/481,015, filed Jun. 9, 2009, now U.S. Pat. No. 7,927,377, issued Apr. 19, 2011, which claims the benefit of U.S. Provisional Application No. 61/131,457 filed Jun. 9, 2008, which are hereby incorporated by reference.

BACKGROUND

The present disclosure is directed to systems for releasably coupling a prosthetic device to the residual limb of an amputee. More specifically, the present disclosure is directed to devices utilizing integrated vacuum and mechanical coupling to provide improved retention and comfort for a prosthetic device including a socket.

SUMMARY

An exemplary elevated vacuum locking system for prosthetic limb may include a plunger pin mounted to a flexible liner and including a through passage between a location proximate the exterior of the liner and a distal end of the plunger pin; a locking mechanism mounted within the distal end of a socket; a manifold mounted to the exterior of the distal end of the socket and including a cavity adapted to receive the distal end of the plunger pin when the patient's residual limb and the liner are installed into the socket, the manifold including a through passage connecting an interior of the cavity to an exterior fitting; and a vacuum pump operative to withdraw air from the interior of the socket via the through passage of the plunger pin, the cavity, and the through passage of the manifold.

In an aspect, a prosthetic limb assembly may include a flexible liner shaped to accept a portion of a patient's residual limb, the flexible liner including an interior and an exterior; a plunger pin mounted to a distal end of the flexible liner, the plunger pin including at least one through passage providing fluidic communication between a location proximate the exterior of the liner and a distal end of the plunger pin; a socket shaped to receive the liner and the patient's residual limb, the socket including a socket interior, a proximal opening for receiving the residual limb, and a distal end including a through hole; a locking mechanism mounted within the distal end of the socket and including a central opening sized to receive the plunger pin, the locking mechanism releasably engaging the plunger pin when the residual limb and the liner are inserted into the socket; a manifold mounted to the exterior of the distal end of the socket, the manifold including a cavity aligned with the through hole in the distal end of the socket, the cavity being adapted to receive the distal end of the plunger pin when the patient's residual limb and the liner are installed into the socket, and the manifold including a through passage fluidicly connecting an interior of the cavity to a fitting mounted on an exterior of the manifold; and a vacuum pump operatively connected to the fitting such that the vacuum pump is operative to withdraw air from the interior of the socket via the through passage of the plunger pin, the cavity, and the through passage of the manifold.

In a detailed embodiment, a prosthetic limb assembly may include a cushion mounted on a proximal surface of the locking mechanism, the cushion including an aperture aligned with the central opening of the locking mechanism and the cushion sealingly engaging the interior of the socket.

In a detailed embodiment, the plunger pin may include a ratchet portion between the liner and the distal end of the plunger pin. In a detailed embodiment, the plunger pin may include a flange interposing the liner and the ratchet portion. In a detailed embodiment, the plunger pin through passage may include a lateral through passage within the flange fluidicly connected to a longitudinal through passage extending from the lateral through passage to the distal end of the plunger pin. In a detailed embodiment, the plunger pin may include a gasket interposing the flange and the locking mechanism when the residual limb and the liner are installed in the socket, the gasket providing a sealed connection between the flange and the locking mechanism.

In a detailed embodiment, the cushion may include at least one flexible rim circumferentially surrounding the cushion, the at least one rim sealingly engaging an inner surface of the socket. In a detailed embodiment, the manifold may include a substantially planar portion mounted to the distal end of the socket and a distally extending projection, the cavity extending from a proximal end of the planar portion and into the projection. In a detailed embodiment, a prosthetic limb assembly may include at least one fastener extending through the manifold, through the socket wall, and into the locking mechanism.

In a detailed embodiment, the manifold may include an integral pyramid coupling. In a detailed embodiment, the pyramid coupling may be adjustable relative to the socket in at least one of anterior-posterior and medial-lateral directions. In a detailed embodiment, an angular orientation of the pyramid coupling may be rotatably adjustable relative to the socket.

In a detailed embodiment, the manifold may include an integral pyramid receiver. In a detailed embodiment, the pyramid receiver may be adjustable relative to the socket in at least one of anterior-posterior and medial-lateral directions. In a detailed embodiment, an angular orientation of the pyramid receiver may be rotatably adjustable relative to the socket.

In a detailed embodiment, a prosthetic limb assembly may include a gasket interposing the manifold and the distal end of the socket. In a detailed embodiment, a prosthetic limb assembly may include a gasket interposing the distal surface of the locking mechanism and the inside distal surface of the socket. In a detailed embodiment, a prosthetic limb assembly may include a gasket interposing the plunger pin and the manifold.

In an aspect, a plunger pin for a prosthetic limb may include a generally cylindrical body having proximal and distal ends; a liner engagement portion adjacent to the proximal end; a locking mechanism engagement portion distal from the proximal end; a flange interposing the liner engagement portion and the locking mechanism engagement portion, the flange extending radially beyond the cylindrical body; an axial through passage extending within the cylindrical body from the distal end to proximate the flange; and at least one radial through passage extending from an edge of the flange to the axial through passage; where the axial through passage and the at least one radial through passage are fluidicly connected within the generally cylindrical body.

In a detailed embodiment, the liner engagement portion may include threads sized to engage corresponding threads on a distal end of a flexible liner sized and shaped to accept a patient's residual limb.

In a detailed embodiment, the locking mechanism engagement portion may include a plurality of circumferential protrusions and recesses. In a detailed embodiment, at least one of the circumferential protrusions and recesses may be tapered.

In a detailed embodiment, a plunger pin may include a gasket surrounding the cylindrical body and adjacent to a distal surface of the flange. In a detailed embodiment, the lateral through passage may include a plurality of lateral through passages fluidically connected to the longitudinal through passage.

In an aspect, a manifold for a prosthetic limb may include a generally planar body having a first side, a second side, and a plurality of edges; a projection extending generally perpendicularly from the second side of the flat body; a cavity having an opening on the first side of the planar body, the cavity extending within the projection; and a passage fluidically connecting the cavity to one of the plurality of edges of the flat body.

In a detailed embodiment, a manifold may include a fitting for coupling to a length of tubing, the fitting being located on the second side of the flat body, where the fitting is fluidically connected to the passage. In a detailed embodiment, a manifold may include a fitting located on the one of the plurality of edges proximate the passage.

In a detailed embodiment, a manifold may include a first annular groove adjacent to and coaxial with the first surface and the cavity. In a detailed embodiment, a manifold may include a second groove on the first surface, the groove circumscribing the cavity and the first groove. In a detailed embodiment, a manifold may include at least one through hole extending from the first surface to the second surface. In a detailed embodiment, a manifold may include a gasket seated within at least one of the first groove and the second groove.

In a detailed embodiment, the projection may include a pyramid coupling. In a detailed embodiment, the projection may include a pyramid receiver.

In an aspect, a method of donning a prosthetic limb may include providing a prosthetic limb having a socket sized and shaped to receive a patient's residual limb, the socket including a locking mechanism including a central opening mounted in a distal end of an interior of the socket; providing a flexible liner, the flexible liner including a distally-mounted plunger pin extending therefrom, the plunger pin including a longitudinal through passage extending from a distal end of the plunger pin to proximate the flexible liner; providing a vacuum pump fluidically coupled to a manifold mounted to a distal exterior surface of the socket, the manifold including a cavity aligned with the central opening of the locking mechanism; providing a sealing sleeve proximate a proximal end of the socket; inserting the patient's residual limb into the flexible liner; inserting the patient's residual limb and the flexible liner into the socket such that the plunger pin enters a central opening in the locking mechanism and the locking mechanism releasably engages the plunger pin; placing the sealing sleeve to create a sealed connection between the flexible liner and the proximal end of the socket; and operating the vacuum pump to withdraw air from within the socket via the longitudinal through passage.

In a detailed embodiment, the plunger pin may include a radially extending flange located proximate the liner, the flange including a lateral through passage fluidically connected to the longitudinal through passage; and the step of operating the pump may include withdrawing air from within the socket via the lateral through passage and the longitudinal through passage. In a detailed embodiment, the plunger pin may include a first gasket adjacent to a distal surface of the flange; and the step of inserting the patient's residual limb and the flexible liner into the socket may include engaging the first gasket with a proximal surface of the locking mechanism. In a detailed embodiment, the cavity may include a second gasket; and the step of inserting the patient's residual limb and the flexible liner into the socket may include engaging the plunger pin and the second gasket.

BRIEF DESCRIPTION OF THE DRAWINGS

The detailed description refers to the following figures in which.

DETAILED DESCRIPTION

Figure 1:
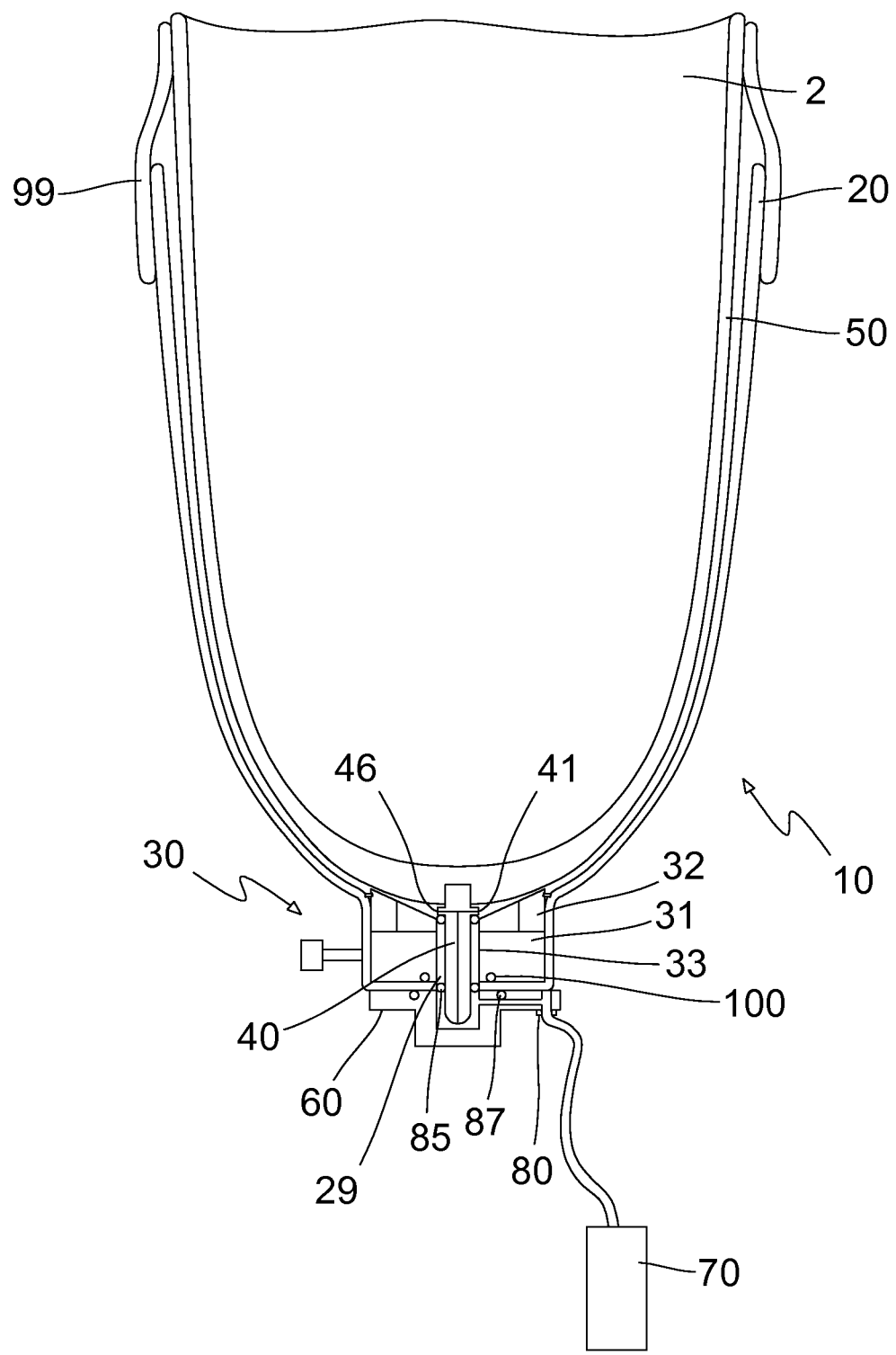
FIG. 1 is a cross-sectional view of an exemplary elevated vacuum locking system.
Figure 2:
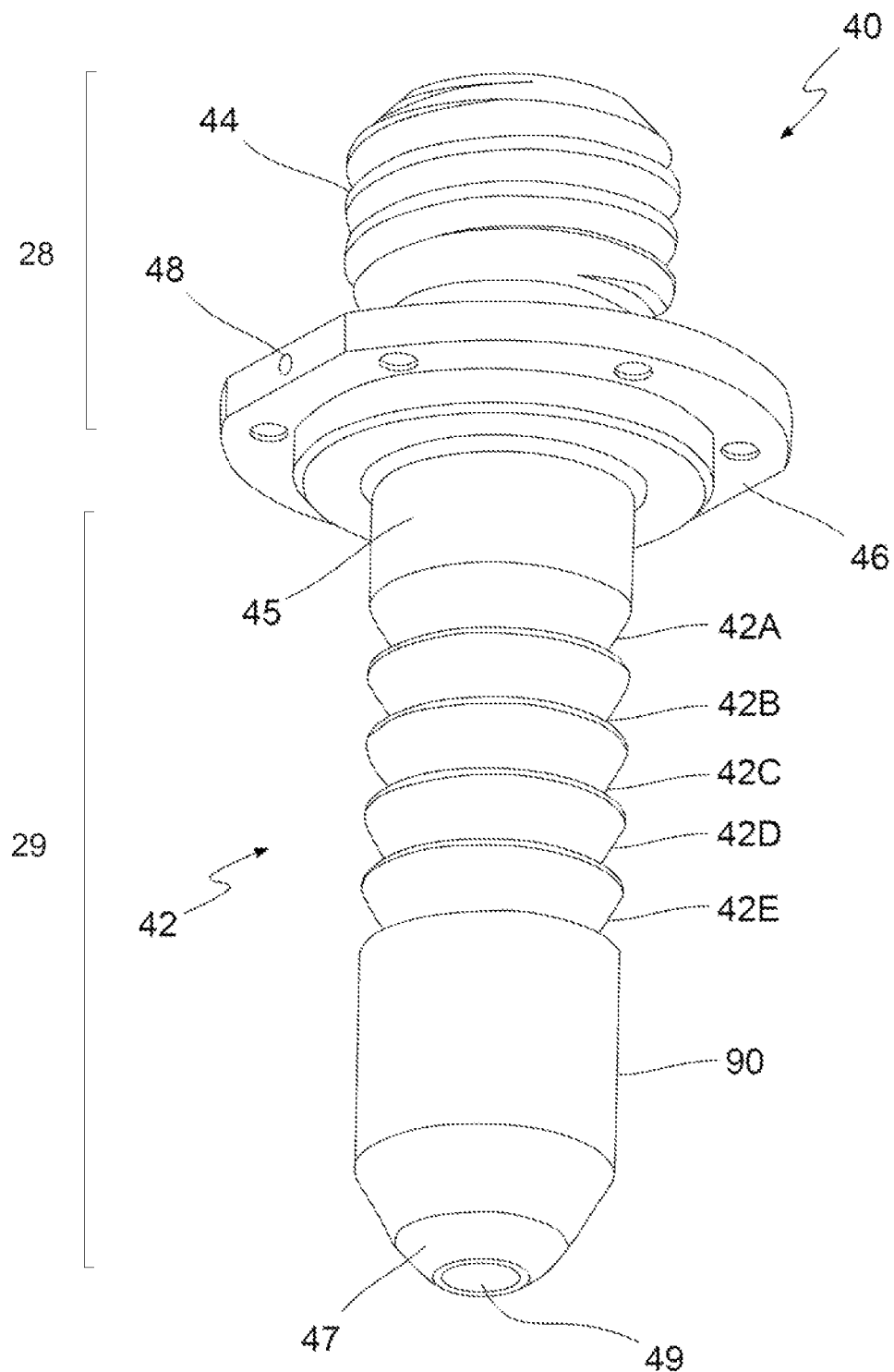
FIG. 2 is a perspective view of an exemplary plunger pin.

As shown in FIG. 1, an exemplary elevated vacuum locking system 10 may include a socket 20 for receiving a portion of an amputee's residual limb 2, a locking mechanism 30 for releasably engaging a plunger pin 40 extending from a flexible liner 50 which interposes residual limb 2 and the socket 20, a manifold 60, a vacuum device 70, and/or a sealing sleeve 99. In an exemplary embodiment, socket 20 may be constructed from a rigid polymer, flexible liner 50 may be formed from a flexible silicone compound, and/or plunger pin 40 and manifold 60 may be constructed from metal, for example.

An exemplary liner 50 may include a fabric shell, such as nylon/cotton sheath/sock that may provide a wicking action to assist in removing air from the socket when the vacuum source is applied. The wick may be provided by a cloth covering on the liner and/or a sock that that may be put on over a liner with no cover, for example. If vacuum is applied without this wick, the liner may seal to the inside surface of the socket and a large portion of air may remain proximal to this sealing point. Using the wick may aid in evacuation of substantially all of the air from the interior of the socket and/or may aid in ensuring that a seal occurs between the sealing sleeve and the portion of the liner proximal to the socket trim line.

FIGS. 2-5 depict an exemplary plunger pin 40 having a generally cylindrical body having proximal and distal ends; a liner engagement portion 28 adjacent to the proximal end; a locking mechanism engagement portion 29 distal from the proximal end; a flange 48 interposing the liner engagement portion 28 and the locking mechanism engagement portion 29. Locking mechanism engagement portion 29 of plunger pin 40 may include a ratchet portion 42 including one or more grooves 42A, 42B, 42C, 42D, 42E arranged circumferentially for releasably engaging the locking mechanism 30. The grooves 42A, 42B, 42C, 42D, 42E may include tapered portions to allow the ratchet portion 42 of the plunger pin 40 to slide relative to a spring-loaded latch in one direction while preventing movement relative to the latch in the opposite direction. In an exemplary embodiment, insertion of the ratchet portion 42 into the locking mechanism 30 may produce one or more audible "clicks," which may indicate positive engagement of the locking mechanism 30 and the plunger pin 40.

Plunger pin 40 may include a liner engagement portion 28 including a threaded end 44 for engaging the flexible liner 50. For example, the threaded end 44 may engage a threaded boss formed within the distal end of flexible liner 50. It is within the scope of the disclosure to utilize other methods of coupling plunger pin 40 to liner 50.

A flange 46 may interpose ratchet portion 42 and threaded end 44. As shown in FIG. 1, flange 46 may be located generally between the locking mechanism 30 and liner 50 when liner 50 is inserted into socket 20.

Figure 3:
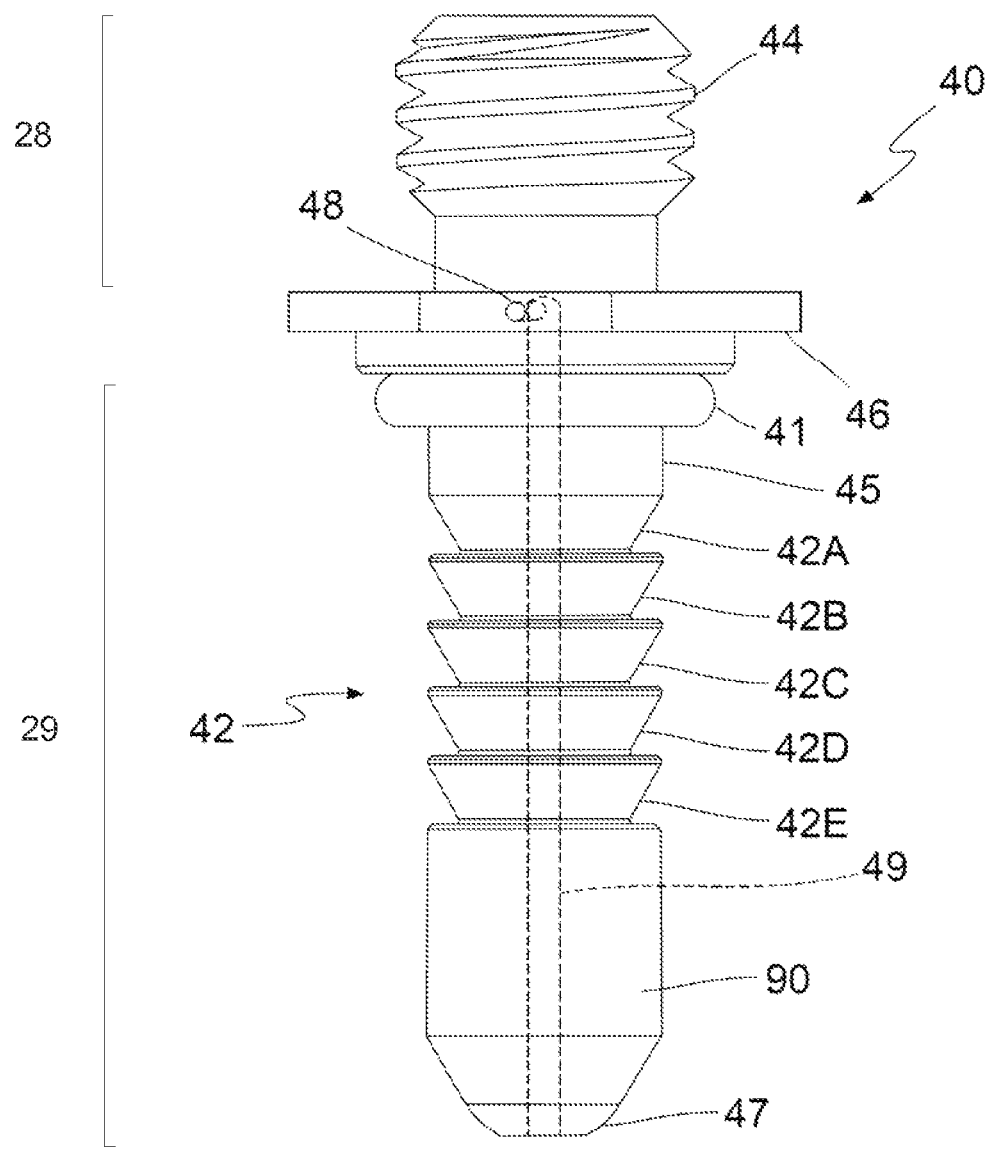
FIG. 3 is an elevation view of an exemplary plunger pin.
Figure 4:
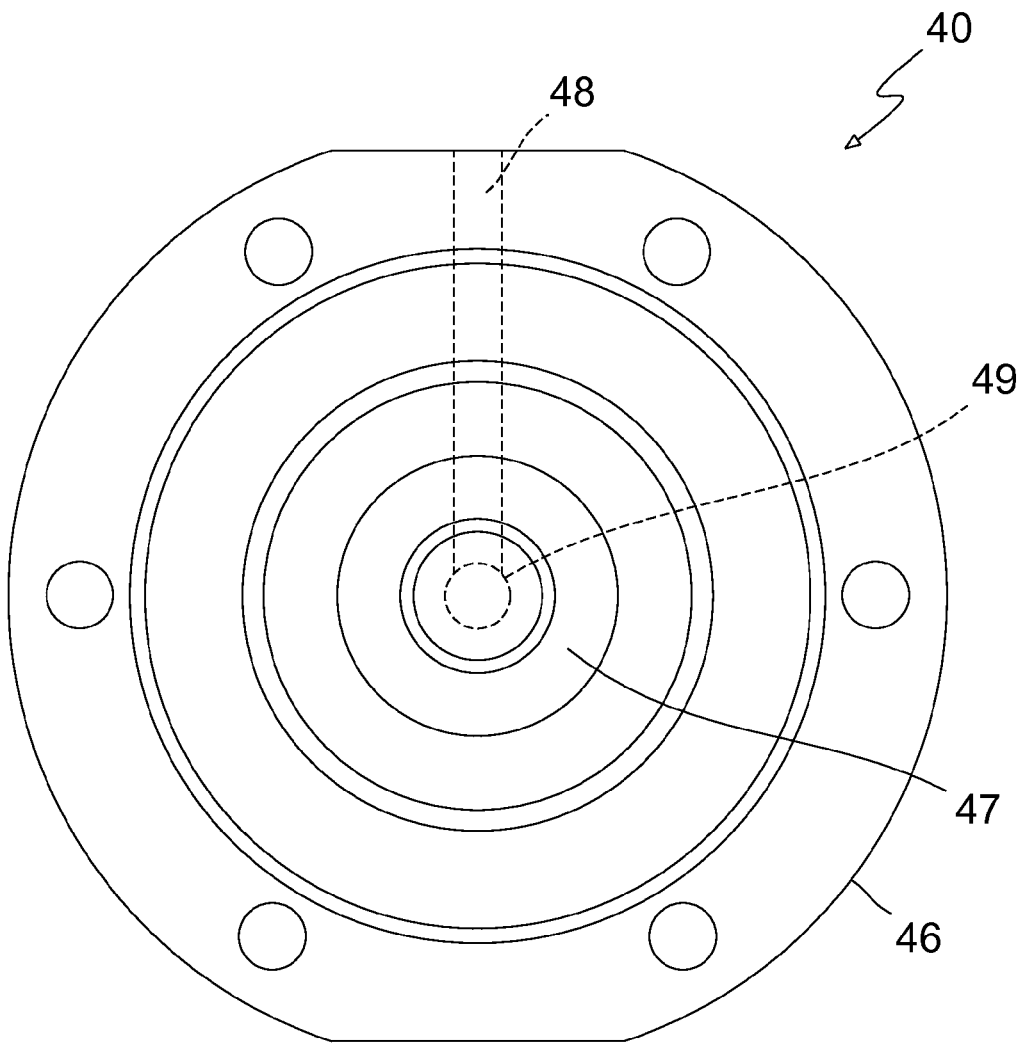
FIG. 4 is a bottom view of an exemplary plunger pin.
Figure 5:
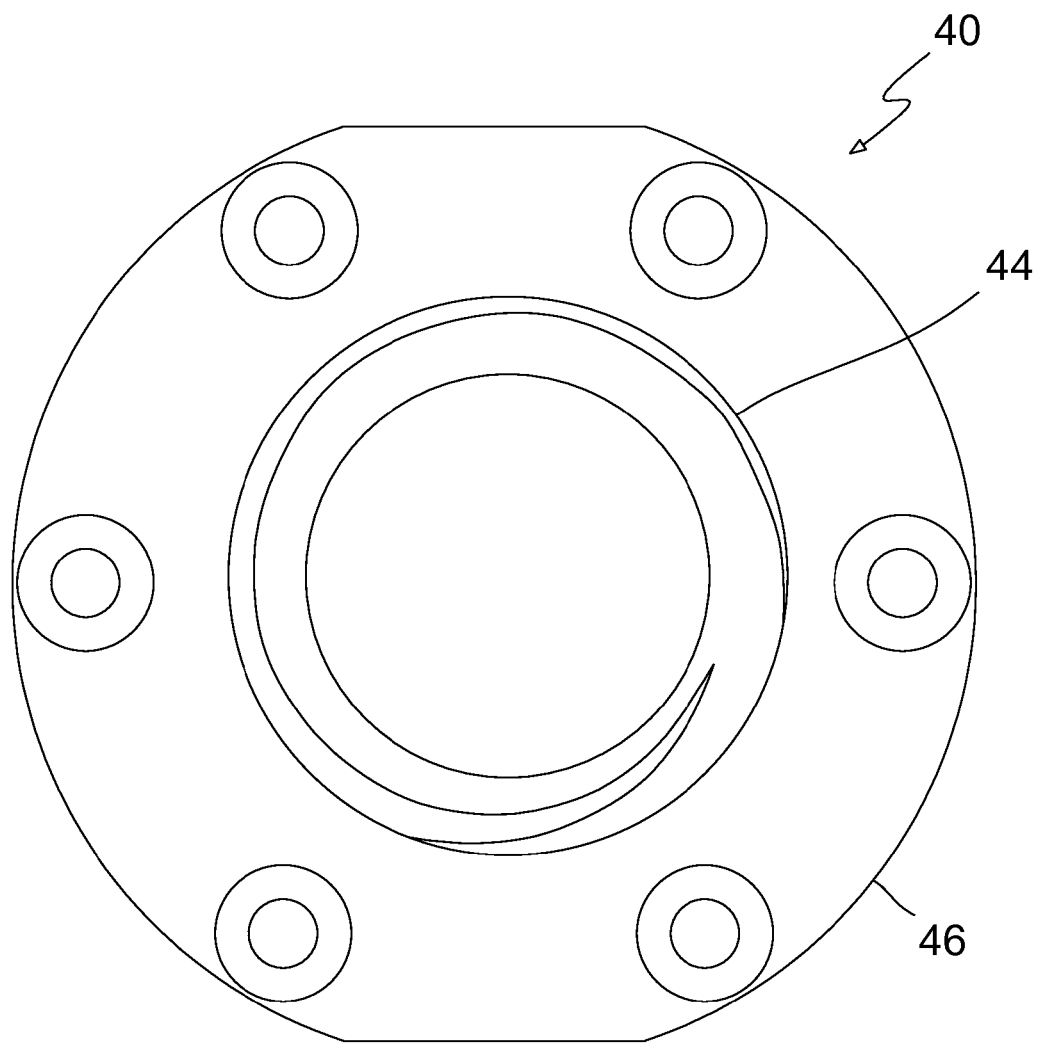
FIG. 5 is a top view of an exemplary plunger pin.
Figure 6:
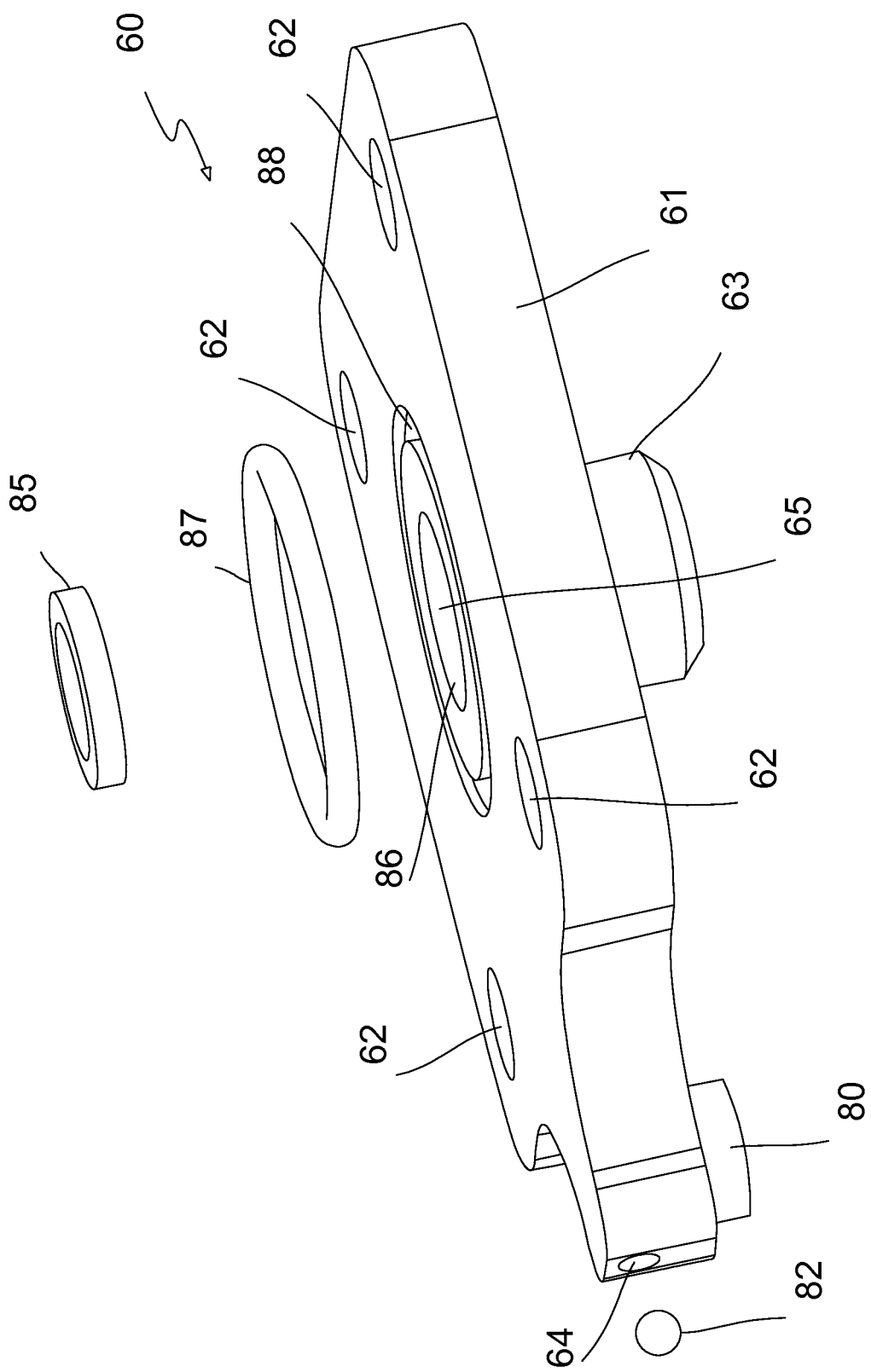
FIG. 6 is an exploded perspective view of an exemplary manifold.
Figure 7:
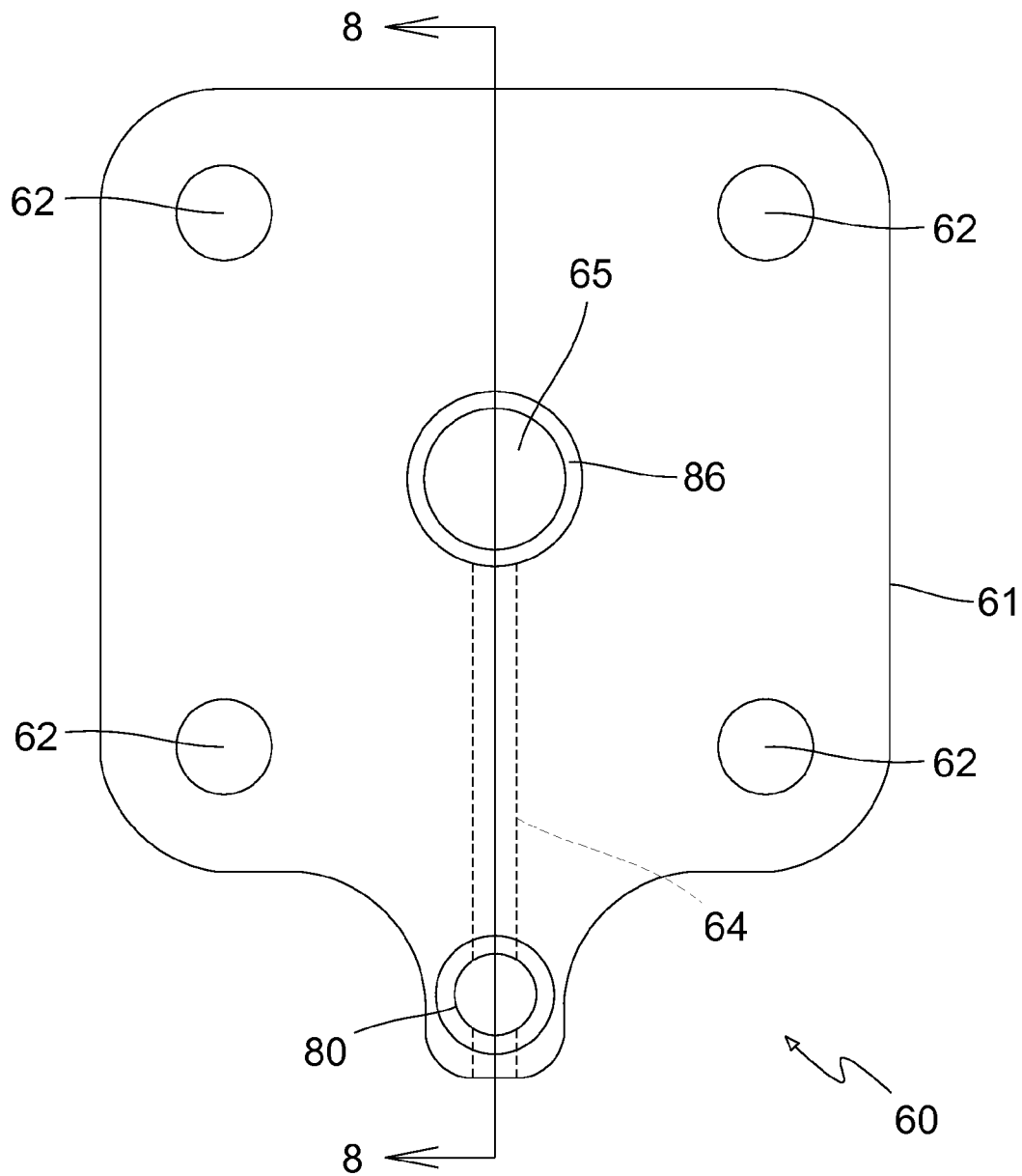
FIG. 7 is a plan view of an exemplary manifold.
Figure 8:
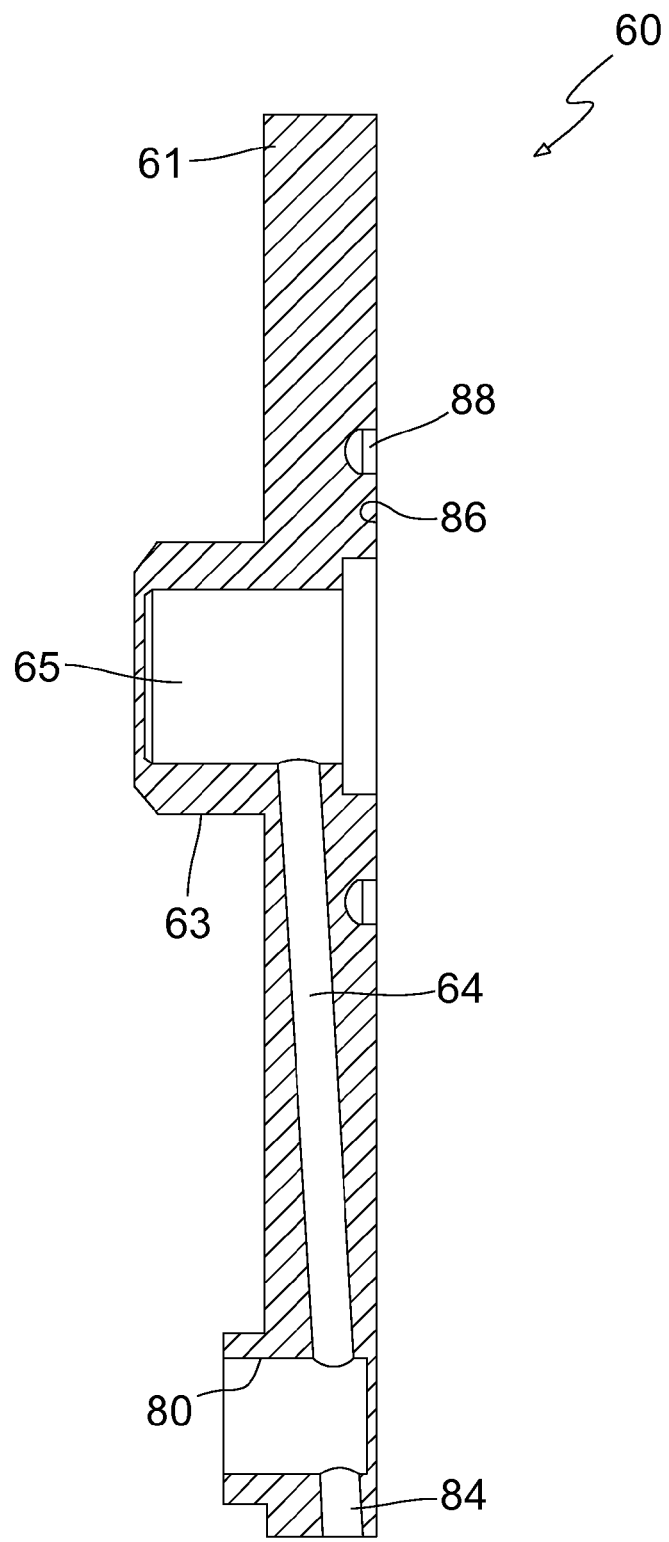
FIG. 8 is a cross-sectional view of an exemplary manifold.
Figure 9:
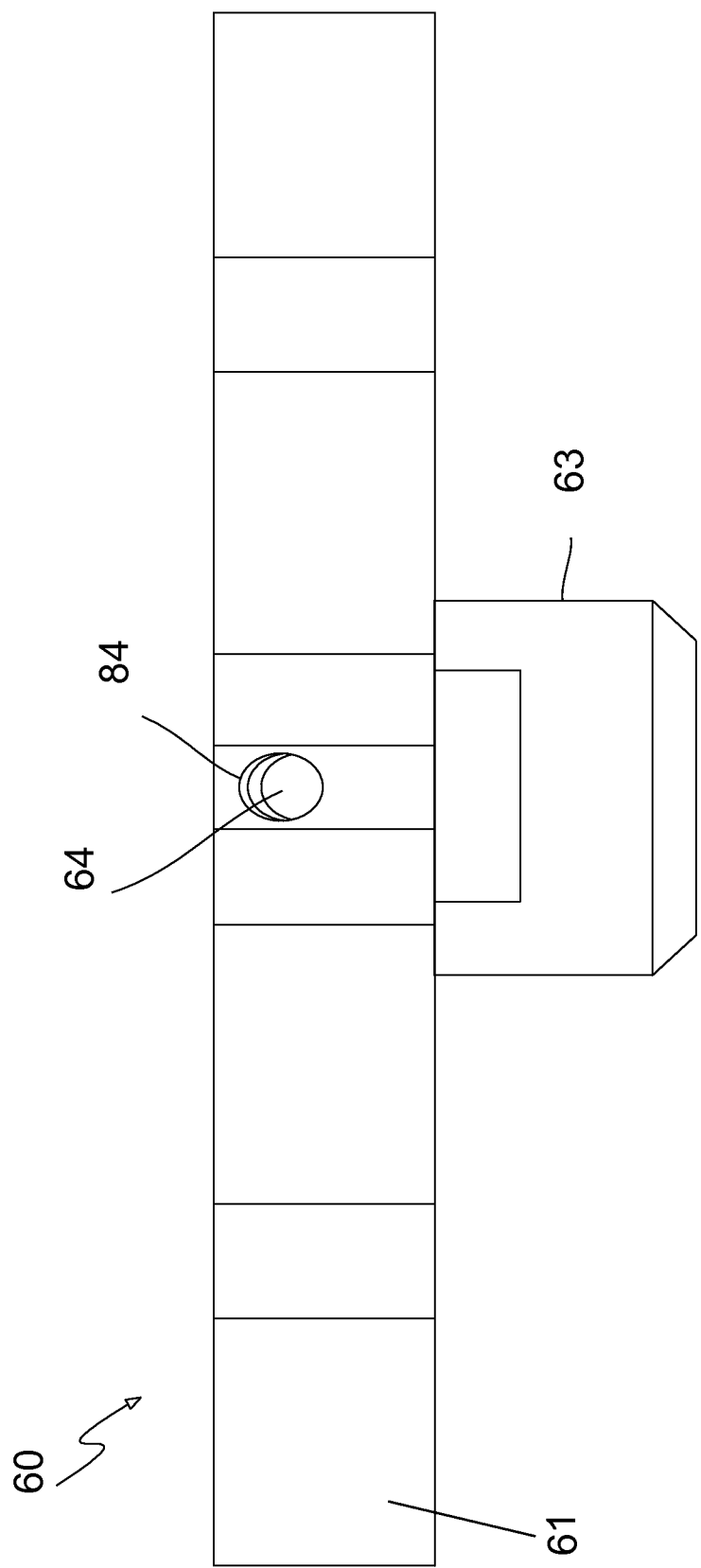
FIG. 9 is an elevation view of an exemplary manifold.

As shown in FIGS. 3 and 4, flange 46 may include a radial passage 48, which may extend generally radially through the flange 46 and which may include a corresponding opening on the diametrically opposite side of flange 46. It is within the scope of the disclosure to incorporate any number of radial passages 48 within the flange 46. Passage 48 may be internally interconnected (in fluid communication) with axial passage 49, which may extend from a distal end 47 of the plunger pin 40 and through the ratchet portion 42.

Exemplary embodiments of the plunger pin 40 may include a gasket 41 (such as an o-ring or a flat washer) which may be seated on an annular surface 45 adjacent to flange 46. Gasket 41 may facilitate a seal between the plunger pin 40 and the locking device 30 as described in greater detail below.

As shown in FIG. 1, when the patient's residual limb 2 and the flexible liner 50 are inserted into the socket 20, the plunger pin 40 may extend through a central hole 33 in the locking device 30, through an opening 29 in the distal end of the socket 20, and into manifold 60 (manifold 60 is depicted in FIGS. 6-9).

Figure 10:
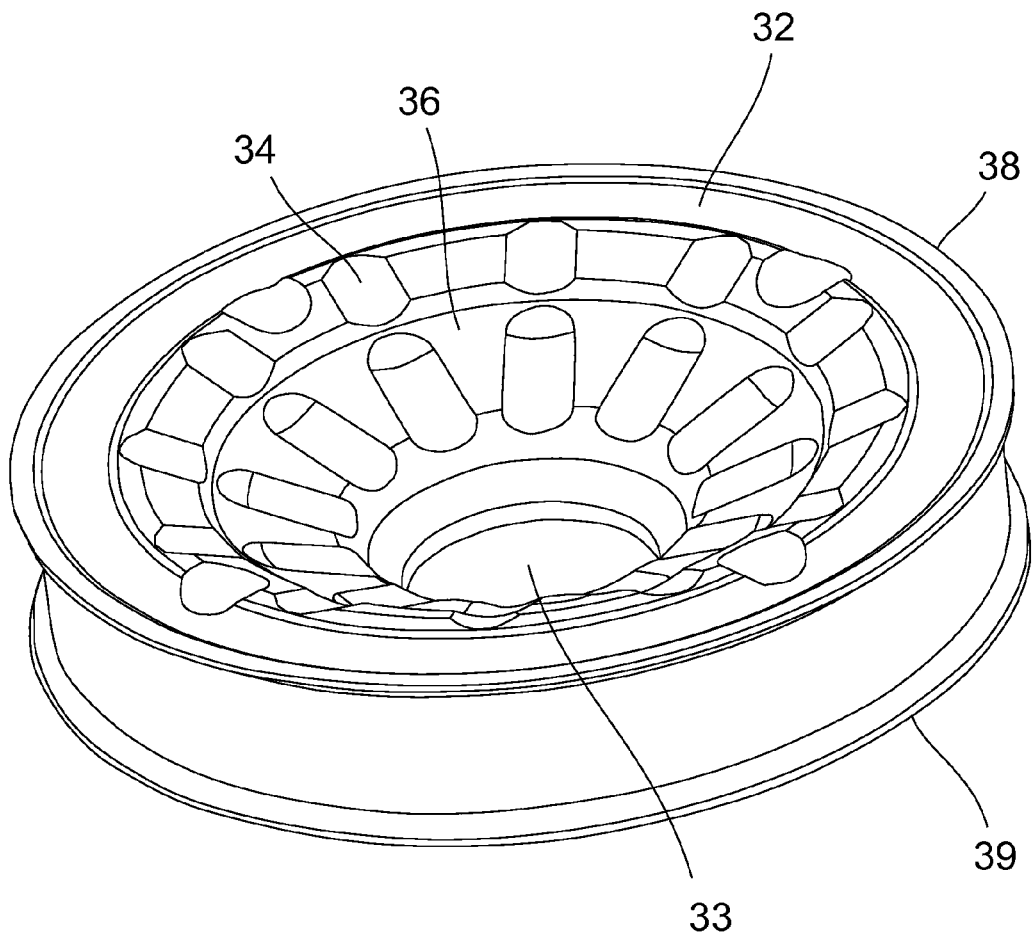
FIG. 10 is a perspective view of an exemplary cushion.
Figure 11:
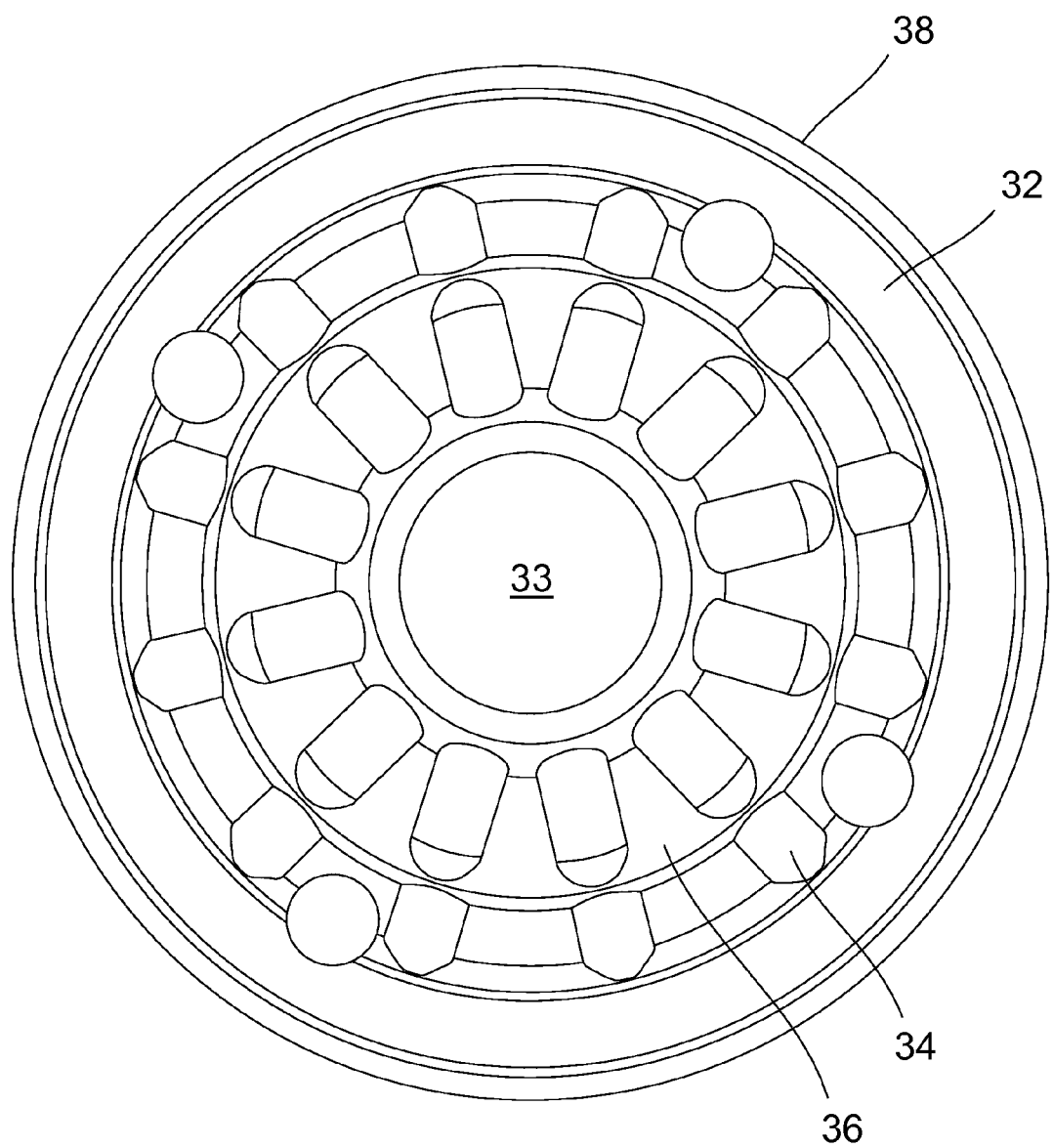
FIG. 11 is a plan view of an exemplary cushion.

Locking device 30, which may include a central hole 33 for receiving the plunger pin 40, may include a lock 31 (such as a shuttle lock sold by Prosthetic Design, Inc. of Clayton, Ohio). The locking device 30 may also include a cushion 32 interposing the liner 50 and the lock 31. As depicted in FIGS. 10-11, cushion 32 may include an aperture 36 (which may be aligned with central hole 33) for receiving the plunger pin 40 as well as one or more guide grooves 34. One or more rims 38, 39 may circumscribe the cushion 32 and may provide a sealing fit between the cushion 32 and the interior of the socket 20. A sealing fit between the cushion 32 and the interior of the socket 20 may be facilitated by a tight engagement of the cushion 32 within the interior of the socket 20, with or without rims 38, 39. The cushion 32 may be constructed from a resilient material, such as urethane.

As depicted in FIGS. 6-9, manifold 60 may include a generally planar portion 61 including one or more mounting holes 62 extending therein for receiving a fastener. Manifold 60 may include a hole 65 sized to receive the distal end of the plunger pin 40. The hole 65 may extend at least partially within a projection 63 extending distally from the planar portion 61 of manifold 60. The planar portion 61 may include a passage 64 extending therethrough, which may extend from a location near the perimeter of the planar portion to the hole 65. Passage 64 may be fluidicly connected to a fitting 80 for coupling with a vacuum device 70.

In the exemplary embodiment depicted in FIGS. 6-9, passage 64 may extend outwardly beyond fitting 80. Ball 82 (a ball bearing, for example) may be fitted within the portion of passage 64 exterior to fitting 80 to seal the outward end of passage 64. Accordingly, any air flowing to or from cavity 65 via passage 64 may flow through fitting 80. It is within the scope of the disclosure to utilize other methods of sealing the exterior end of passage 64, such as a threaded plug and/or a plug retained by an adhesive, for example.

Figure 14:
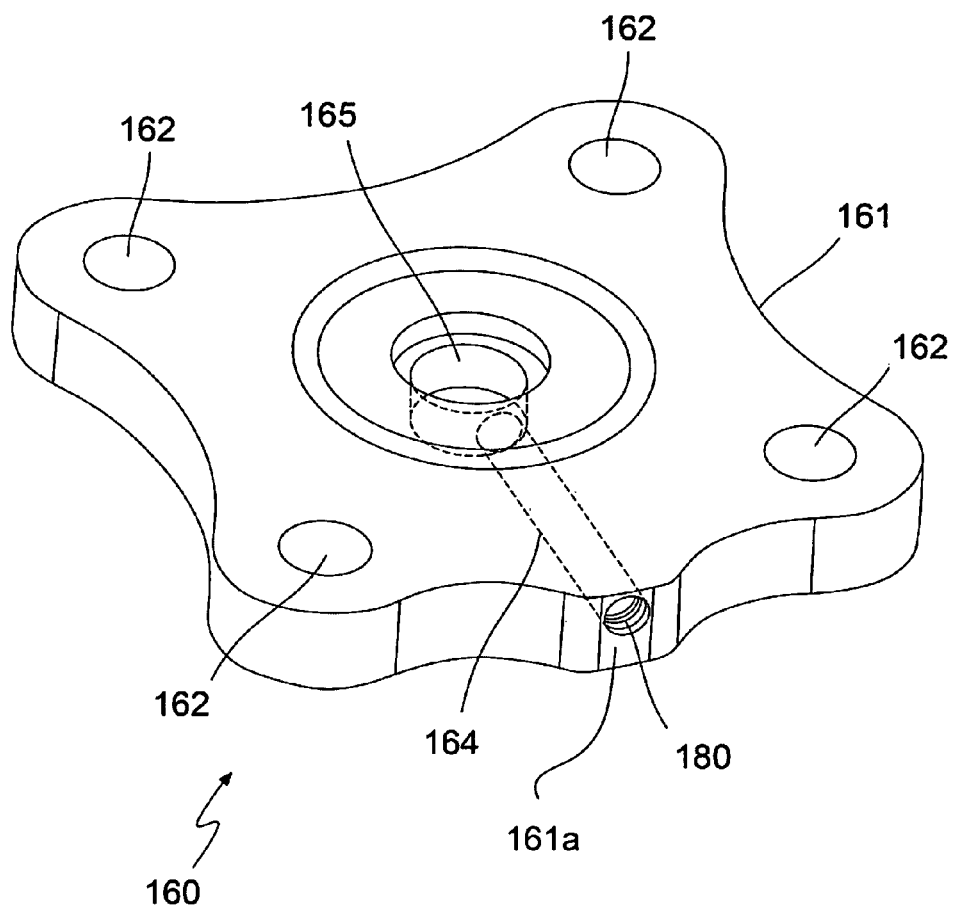
FIG. 14 is a perspective view of an alternative exemplary manifold, all in accordance with at least some aspects of the present disclosure.

FIG. 14 depicts an alternative exemplary embodiment manifold 160 which may include a hole 165 for receiving the plunger pin 40, mounting holes 162, and a planar portion 161 similar to those described with reference to manifold 60. In this exemplary embodiment, fitting 180 may be located generally in line with passage 164 extending from edge 161a of planar portion 161, thus obviating the need to seal an exterior end of passage 64. Fitting 180 is located on edge 161a of planar portion 161 proximate the passage 164.

Referring back to FIGS. 6-9, a gasket 85 (such as an o-ring or flat washer) may be provided to seal the interface between the hole 65 and the plunger pin 40. In the exemplary manifold 60 shown in FIGS. 6-9, gasket 85 may be mounted within an annular groove 86 on planar portion 61 of manifold 60 and coaxial with the hold 65. Gasket 85 extends radially inward into hole 65 and engages plunger pin 40 when the patient's residual limb 2 and liner 50 are inserted into the socket 20. In particular, gasket 85 may engage surface 90 of plunger pin 40.

A gasket 87 (such as an o-ring or flat washer) may be provided to seal the interface between the exterior distal surface of the socket 20 and the manifold 60. In the exemplary manifold 60 shown in FIGS. 6-9, gasket 87 may be mounted within an annular groove 88 on the proximal surface of planar portion 61 of manifold 60. It is within the scope of the disclosure to provide a similar groove on the distal exterior socket 20 in addition to or in place of groove 88. In addition, exemplary embodiments may include a gasket on the distal surface of the locking mechanism 30 and this gasket may be located within a groove on the locking mechanism 30 and/or the interior of the socket 20.

Vacuum device 70 may comprise any device capable of withdrawing air from within the socket 20. For example, vacuum device 70 may comprise a battery-powered, electrically operated pump. Vacuum device 70 may be mounted on the prosthesis or elsewhere (such as on the patient's body) and may include a mechanism for monitoring and maintaining a desired level of vacuum within the socket. For example, vacuum device 70 may be mounted on an upright assembly of a prosthesis. In an exemplary embodiment, vacuum device 70 may be set to maintain vacuum within the socket at, for example, 20-24 in Hg. The vacuum device 70 may be fluidicly connected to fitting 80 on manifold 60 by, for example, flexible tubing and appropriate fittings. It is within the scope of the disclosure to utilize other vacuum devices, such as a hand-operated vacuum pump.

Figure 12:
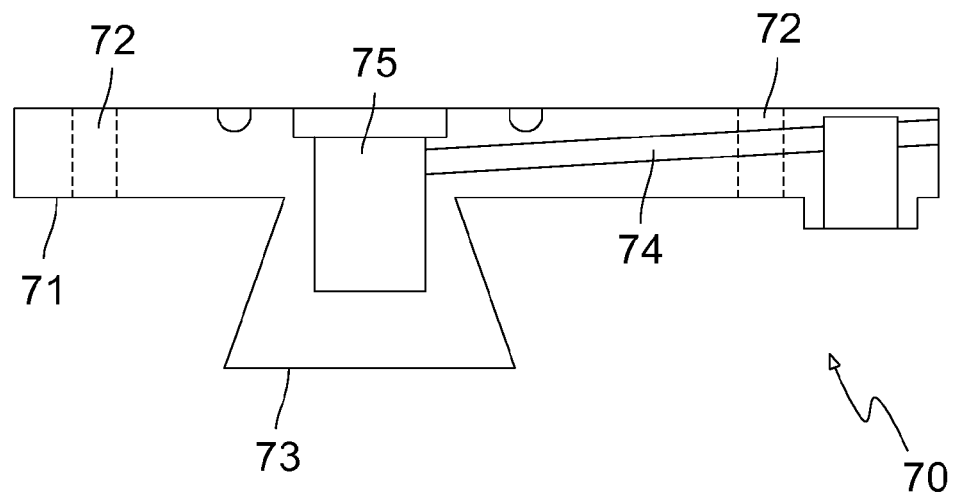
FIG. 12 is a cross-sectional view of an alternative exemplary manifold.

It is within the scope of the disclosure to incorporate a coupling into the manifold adapted to couple to other prosthetic limb components (such as knee components, shin components, and the like). For example, as shown in FIG. 12, an exemplary manifold 70 may include a pyramid 73 for attaching additional components of a prosthesis. Manifold 70 may include a planar portion 71, mounting holes 72, a passage 74, and a hole 75 for receiving the plunger pin, as well as other features generally similar to the corresponding components of manifold 60. A manifold 70 including a pyramid 73 may allow construction of a prosthesis having a smaller overall height than an embodiment having separate manifold and pyramid components. The pyramid 73 may incorporate any known features of pyramids (such as an adjustable lateral position and/or a rotatably adjustable orientation). See, for example, the pyramids sold by Prosthetic Design, Inc. of Clayton, Ohio.

Figure 13:
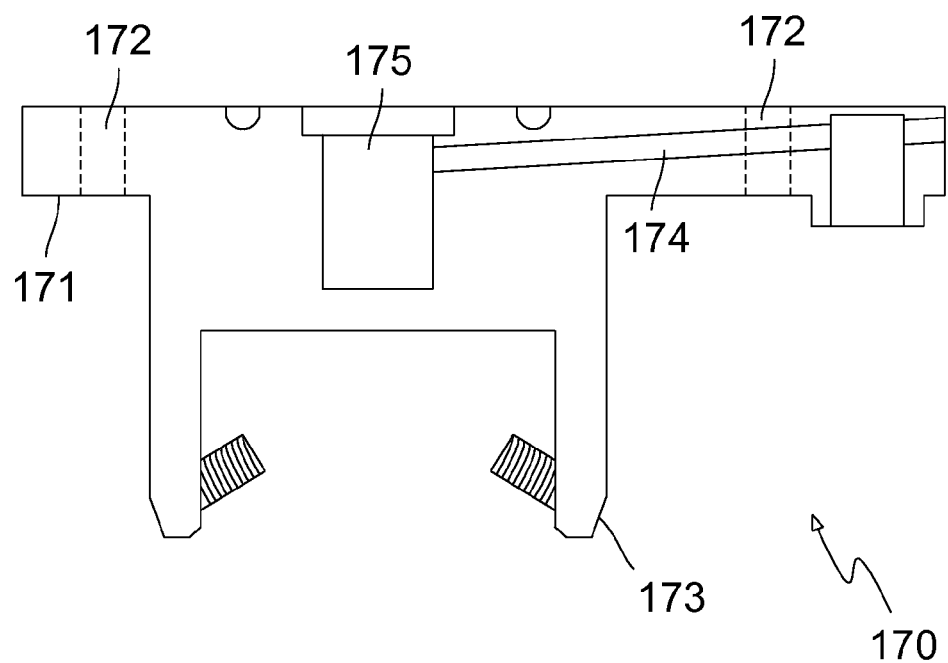
FIG. 13 is a cross sectional view of an alternative exemplary manifold.

FIG. 13 depicts another exemplary manifold 170 which may include a pyramid receiver 173 for attaching additional components of a prosthesis, such as a prosthetic lower leg and foot assembly. Similar to manifold 70 shown in FIG. 12, manifold 170 may include a planar portion 171, mounting holes 172, a passage 174, and a hole 175 for receiving a plunger pin, as well as other features generally similar to the corresponding components of manifold 60. A manifold 170 including a pyramid receiver may allow construction of a prosthesis having a smaller overall height than an embodiment include separate manifold and pyramid components. The pyramid 173 may incorporate any known features of pyramid receivers (such as an adjustable lateral position and/or a rotatably adjustable orientation). See, for example, the pyramid receivers sold by Prosthetic Design, Inc. of Clayton, Ohio. It is within the scope of the disclosure to incorporate any known coupling into the manifold and to use the coupling to attach components of the prosthetic device, for example.

Exemplary embodiments may be utilized as follows. The amputee may don the flexible liner 50 over her residual limb 2. She may insert the residual limb 2 into the socket 20, allowing the plunger pin 40 to enter the locking mechanism 30. Air displaced by the insertion of the residual limb 2 into the socket 20 may be vented via any gaps present between the liner 50 and the proximal end of the socket 20. Once residual limb 2 is fully inserted into socket 20, flange 46 of plunger pin 40 may compress gasket 41 against a proximal surface of the locking mechanism 30. The amputee may roll a sealing sleeve 99 such that it seals the proximal opening of the socket 20 to the liner 50.

With the residual limb 2 and liner 50 fully inserted into the socket, a sealed volume is created between the exterior surface of the liner 50 and the interior surface 20 of the socket. The proximal end of socket 20 is sealed to liner 50 using, for example, a sealing sleeve 99. The distal end of socket 20 is sealed to the perimeter of cushion 32. Cushion 32 is sealed to locking mechanism 30, which is sealingly engaged with plunger pin 40 by gasket 41. Thus, passages 48, 49 through plunger pin 40 provide the only path for fluidic communication with the sealed volume. In addition, the sealing engagement of gasket 85 with shoulder 90 of plunger pin 40 creates a sealed connection between the sealed volume within the socket and fitting 80. Accordingly, a vacuum applied at fitting 80 draws air from within the sealed volume.

In addition, as discussed above, gasket 87 provides a seal between the exterior distal surface of socket 20 and manifold 60. One or more gaskets or seals may be provided on the latching pin of the locking mechanism 30 to prevent air leakage into central opening 33 of locking mechanism 30 via the internal components of locking mechanism 30. Other locking devices may be sealed in a similar manner using appropriate gaskets or seals. Accordingly, if one or both of gaskets 41, 85 fails, if plunger pin 40 is not fully inserted into locking mechanism 30, or if plunger pin 40 is absent, a sealed connection between the interior of socket 20 and fitting 80 is provided. Specifically, the proximal end of socket 20 is sealed to liner 50 using sealing sleeve 99, the outer circumference of cushion 32 is sealed to the interior of socket 20, cushion 32 is sealed to locking mechanism 30, the latching pin of the locking mechanism 30 is sealed using a gasket, a gasket 100 may provide a seal between the distal surface of the locking mechanism 30 and the interior of the socket 20, and manifold 60 is sealed to the exterior distal end of the socket 20 using gasket 87.

The amputee may operate the vacuum device 70 to withdraw air from within the socket 20. Air within the socket 20 may be withdrawn through passages 48, 49 of the plunger pin 40, hole 65, and passage 64.

To remove the prosthesis, the amputee may turn off the vacuum device 70. The amputee may roll the sealing sleeve 99, thereby providing an air inlet path into the socket 20 via the proximal end of the socket 20. The amputee may withdraw her residual limb 2 from the socket 20 by releasing the locking mechanism 30 (such as by depressing or withdrawing a pin which disengages a latch from the ratchet portion 42 of the plunger pin 40).

An exemplary vacuum device 70 may be adapted to maintain a desired vacuum level within the socket 20, thereby retaining the residual limb 2 within the socket 20. For example, the vacuum device may include one or more pressure sensors and a control circuit that selectively energizes an electrically driven vacuum pump to maintain the desired vacuum level within the socket. This vacuum retention capability may provide advantages known in the art, such as improved comfort and prevention of excessive fluid loss from the residual limb 2.

In the event of a failure of the vacuum device 70 or leakage of air into the socket 20 (or any other cause of loss of vacuum within the socket), the plunger pin 40 and locking mechanism 30 may retain the residual limb 2 within the socket 20. This mechanical backup capability may provide improved safety and reliability, as well as peace of mind for the amputee.

While exemplary embodiments have been set forth above for the purpose of disclosure, modifications of the disclosed embodiments as well as other embodiments thereof may occur to those skilled in the art. Accordingly, it is to be understood that the disclosure is not limited to the above precise embodiments and that changes may be made without departing from the scope. Likewise, it is to be understood that it is not necessary to meet any or all of the stated advantages or objects disclosed herein to fall within the scope of the disclosure, since inherent and/or unforeseen advantages may exist even though they may not have been explicitly discussed herein.

What is claimed is:

1. A plunger pin for a prosthetic limb comprising:
   a generally cylindrical body having proximal and distal ends;
   a liner engagement portion adjacent to the proximal end;
   a locking mechanism engagement portion distal from the proximal end;
   a flange interposing the liner engagement portion and the locking mechanism engagement portion, the flange extending radially beyond the cylindrical body;
   an axial through passage extending within the cylindrical body from the distal end to proximate the flange; and
   at least one radial through passage extending from an edge of the flange to the axial through passage;
   wherein the axial through passage and the at least one radial through passage are fluidicly connected within the generally cylindrical body.

2. The plunger pin of claim 1, wherein the liner engagement portion includes threads sized to engage corresponding threads on a distal end of a flexible liner sized and shaped to accept a patient's residual limb.

3. The plunger pin of claim 1, wherein the locking mechanism engagement portion includes a plurality of circumferential protrusions and recesses.

4. The plunger pin of claim 3, wherein at least one of the circumferential protrusions and recesses is tapered.

5. The plunger pin of claim 1, further comprising a gasket surrounding the cylindrical body and adjacent to a distal surface of the flange.

6. The plunger pin of claim 1, wherein the at least one lateral through passage includes a plurality of lateral through passages fluidicly connected to the longitudinal through passage.

7. A manifold for a prosthetic limb comprising:
- a generally planar body having a first side, a second side, and a plurality of edges;
- a projection extending generally perpendicularly from the second side of the flat body;
- a cavity having an opening on the first side of the planar body, the cavity extending within the projection;
- a passage fluidicly connecting the cavity to one of the plurality of edges of the flat body; and
- a fitting for coupling to a length of tubing, the fitting being located on the second side of the flat body, where the fitting is fluidicly connected to the passage.

8. The manifold of claim 7, wherein the projection includes a pyramid coupling.

9. The manifold of claim 7, wherein the projection includes a pyramid receiver.

10. A manifold for a prosthetic limb comprising:
- a generally planar body having a first side, a second side, and a plurality of edges;
- a projection extending generally perpendicularly from the second side of the flat body;
- a cavity having an opening on the first side of the planar body, the cavity extending within the projection;
- a passage fluidicly connecting the cavity to one of the plurality of edges of the flat body; and
- a first annular groove adjacent to and coaxial with the first surface and the cavity.

11. The manifold of claim 10, further comprising a fitting located on the one of the plurality of edges proximate the passage.

12. The manifold of claim 10, further comprising a second groove on the first surface, the groove circumscribing the cavity and the first groove.

13. The manifold of claim 12, further comprising at least one through hole extending from the first surface to the second surface.

14. The manifold of claim 12, further comprising a gasket seated within at least one of the first groove and the second groove.

15. The manifold of claim 10, wherein the projection includes a pyramid coupling.

16. The manifold of claim 10, wherein the projection includes a pyramid receiver.

* * * * *